United States Patent [19]

Harris et al.

[11] 4,279,890

[45] Jul. 21, 1981

[54] COSMETIC FACIAL POWDER CONTAINING WALNUT SHELL FLOUR

[75] Inventors: Thomas C. Harris, Paterson; Arthur Georgalas, Leonardo, both of N.J.

[73] Assignee: Chattem, Inc., Chattanooga, Tenn.

[21] Appl. No.: 799,229

[22] Filed: May 23, 1977

Related U.S. Application Data

[63] Continuation of Ser. No. 620,731, Oct. 8, 1975, abandoned.

[51] Int. Cl.$^3$ .............................................. A61K 7/021
[52] U.S. Cl. ................................. 424/69; 424/63; 424/357; 424/364
[58] Field of Search .......................... 424/69, 357, 364

[56] References Cited

U.S. PATENT DOCUMENTS

| | | | |
|---|---|---|---|
| 3,196,079 | 7/1965 | Blaustein | 424/69 X |
| 3,278,383 | 10/1966 | White | 424/69 |
| 3,800,034 | 3/1974 | Kircher | 424/69 |

OTHER PUBLICATIONS

Blanton, Chem. Abs., 1956, vol. 50, p. 9676d.
Rohm & Haas, Chem. Abs., 1966, vol. 64, p. 19336b.
Handbook of Insecticide Dust Diluent & Carriers, 1955, Watkins et al., pp. 42 to 45.
The Dispensatory of the U.S.A., 22nd Edition, 1937, Part II, pp. 1431 to 1432.

*Primary Examiner*—Dale R. Ore
*Attorney, Agent, or Firm*—Hill, Van Santen, Steadman, Chiara & Simpson

[57] ABSTRACT

A cosmetic facial powder composition including filler, mendicant and fragrance ingredients possesses a high degree of transparency and oil absorbency provided by a large amount of the filler content being walnut shell flour having a particle size of not more than about 40 microns. The composition may be in loose or compact powder form.

10 Claims, No Drawings

COSMETIC FACIAL POWDER CONTAINING WALNUT SHELL FLOUR

This is a continuation of Ser. No. 620,731, filed Oct. 8, 1975, now abandoned.

BACKGROUND OF THE INVENTION

This invention relates to improved walnut shell flour based powder compositions having good adsorption of body fluids. More particularly, it relates to walnut shell flour based face powder compositions.

Cosmetic powders having oil absorption properties have conventionally used a major proportion of talc. Talc, however, has certain disadvantages. For instance, when wetted with water and dried it forms hard agglomerates which are irritating to the skin. This property is reduced by replacing some of the talc with cornstarch, but cornstarch is an excellent medium for bacterial growth and is thereby another source of irritation.

White et al (U.S. Pat. No. 3,278,383) disclose topical therapeutic powder compositions containing a major proportion of finely divided alpha cellulose. The powders are alleged to be non-staining, highly absorbent, soft and smooth, free of starch and boric acid and completely non-caking and non-crusting. The White et al compositions contain bacteriostatic and fungistatic agents and are primarily baby powders.

While corn cob dust or corn cob flour or finely divided alpha cellulose have the essential properties required, they have a tendency to rot, causing them to change to a gray powder which is not readily colored to achieve an acceptable skin tone. Moreover, corn cob dust or corn cob flour is becoming increasingly less available since it is being used in the manufacture of furfural; it is also being used in the grain alcohol industry and as a carrier for pesticides.

Walnut shell flour on the other hand is readily available, has properties very similar to corn cob dust or corn cob flour and, in addition, has a more consistent color and can be converted readily, by the addition of small amounts of coloring materials, such as iron oxides (red, yellow and brown), ultramarine blue, etc., to a universal skin tone or the like. This has considerable advantage in facial powders.

Walnut shell flour is obtained in fine particle size ($<40\mu$) and is more transparent than talc or kaolin. However, it is readily used in combination therewith to provide face powders with a high degree of transparency and oil absorbency. In addition, walnut shell flour is more readily compacted than corn cob dust or corn cob flour. This is a desirable factor in the preparation of compacted or pressed face powders.

Particle size is important in face powder preparations since the walnut shell flour becomes less transparent, rougher, more dusty, loses absorption and becomes less compactible as the particle size increases. Thus, the compositions of the present invention preferable utilize finely divided walnut shell flour, i.e. having a particle size less than about 30 microns.

The face powder compositions of the present invention may contain in addition to walnut shell flour other fillers, such as talc, kaolin, tatanium coated mica, and the like, to provide additional absorption of body oils and moisture. Total filler content of the powders ranges from about 90% to 99%, while the walnut shell flour content will vary from about 30% to 99%, and preferably from about 30% to 60% for loose powders and 40% to 80% for pressed powders.

The compositions may also contain metallic stearates, such as zinc or magnesium stearates, to assist in skin adhesion, and as a binder. In addition, they provide a smooth, supple feel.

Medicaments, e.g., fungicides, such as Vancide 89RE, N-(trichloromethylmercapto)-4-cyclohexane 1,2-dicarboximide; binders, such as triethyl citrate, mineral oil or polyethylene glycol stearates; colorants, such as red, yellow, and brown oxides; fragrances, and the like, may also be included in the composition.

The following examples are provided for illustrative purposes and may include particular features of the invention. However, the examples should not be construed as limiting the invention, many variations of which are possible without departing from the spirit or scope thereof.

EXAMPLE 1

A loose face powder composition was prepared as follows:

|  | Parts by Weight |
|---|---|
| Walnut shell flour (particle size $<30\mu$) | 40.00 |
| Mica, titanium coated | 5.00 |
| Magnesium stearate | 4.00 |
| Mica #221* | 49.25 |
| Vancide 84RE | 0.25 |
| Colorants | 0.75 |
| Perfume | 0.75 |
|  | 100.00 |

*ground mica, ~80 microns

EXAMPLE 2

A pressed face powder formulation was prepared as follows:

|  | Parts by Weight |
|---|---|
| Walnut shell flour (WF-9) | 70.00 |
| Talc (WC&D#1615) | 12.60 |
| Magnesium stearate | 2.00 |
| Kaolin ASP 200 | 5.00 |
| Titanium coated mica | 5.00 |
| Vancide 89RE | 0.25 |
| Colorants | 0.65 |
| PEG 400 monostearate | 0.75 |
| Triethyl citrate | 3.25 |
| Fragrance | 0.50 |
|  | 100.00 |

EXAMPLE 3

Evaluation of Oil Absorption Properties Versus Competitive Products

|  | Grams Oil % Absorption (Gram Powder × 100) |
|---|---|
| Loose powder of Example 1 | 84 |
| Revlon #223 | 44 |
| Coty | 40 |
| Du Barry #241128 | 34 |
| Max Factor #202 | 42 |
| Almay #202 | 38 |
| Pressed powder of Example 2 | 68 |
| Almay, Pure Beauty | 41.3 |
| Cover Girl (Noxell) | 23.3 |

-continued

| | Grams Oil % Absorption (Gram Powder × 100) |
|---|---|
| Max Factor (Creme Puff) | 28 |
| Revlon (Love Pat) | 32.6 |

We claim:

1. A loose face powder composition which comprises about 40 percent by weight walnut shell flour having a particle size less than 30 microns, about five percent by weight titanium coated mica, about four percent by weight magnesium stearate, about 49.25 percent by weight ground mica of not more than about 80 microns, and the balance selected from the group consisting of a fungicide, a colorant, and a perfume.

2. A pressed face powder formulation composed of about 70 percent by weight walnut shell flour having a particle size of not more than about 40 microns, about 12.6 percent by weight talc, about 2 percent by weight magnesium stearate, about five percent by weight kaolin, about five percent by weight titanium coated mica, and the balance selected from the group consisting of a fungicide, a colorant, a binder, and a fragrance.

3. In a compacted facial powder composition having a high degree of transparency and oil absorbency, the improvement which comprises the inclusion thereof from about 40 to 80% by weight of walnut shell flour having a particle size of not more than 40 microns.

4. The composition of claim 3 which also includes at least one member selected from the group consisting of a fungicide, a binder, and a colorant.

5. The composition of claim 3 wherein the walnut shell flour has a particle size of less than about 30 microns.

6. The composition of claim 3 including a filler selected from the group consisting of talc, kaolin, mica, a metallic stearate and a mixture thereof.

7. In a loose facial powder composition having a high degree of transparency and oil absorbency, the improvement which comprises the inclusion thereof from about 30 to about 60% by weight of walnut shell flour having a particle size of not more than 30 microns.

8. The composition of claim 7 including at least one member selected from the group consisting of a fungicide, a binder and a colorant.

9. The composition of claim 7 including a filler selected from the group consisting of talc, kaolin, mica, a metal stearate and a mixture thereof.

10. In an absorbent cosmetic facial powder composition for application to the human face and having high absorbency for facial oils and moisture, the improvement which comprises the inclusion thereof from 30 to 99% walnut shell flour having a particle size of not more than about 40 microns.

* * * * *